United States Patent [19]
Harmon

[11] Patent Number: 5,772,671
[45] Date of Patent: Jun. 30, 1998

[54] DEVICE FOR IMPLANTING ARTICLES UNDER SKIN

[75] Inventor: John C. Harmon, Eau Galle, Wis.

[73] Assignee: Mark L. Anderson, Spring Valley, Wis.

[21] Appl. No.: 782,125

[22] Filed: Jan. 13, 1997

[51] Int. Cl.$^6$ .......................... A61B 17/00; A61M 31/00
[52] U.S. Cl. .............................................. 606/117; 604/60
[58] Field of Search ............................... 606/1, 116, 117;
604/51, 57, 60, 59, 164, 165, 220, 272, 116

[56] References Cited

U.S. PATENT DOCUMENTS

| | | | |
|---|---|---|---|
| 2,007,626 | 7/1935 | Waring | 604/59 |
| 5,211,129 | 5/1993 | Taylor et al. . | |
| 5,250,026 | 10/1993 | Ehrlich et al. . | |
| 5,507,807 | 4/1996 | Shippert | 604/59 |

FOREIGN PATENT DOCUMENTS 0957399  2/1950  France ..................................... 604/59

*Primary Examiner*—Glenn K. Dawson
*Attorney, Agent, or Firm*—Skinner And Associates

[57] ABSTRACT

An implanter for inserting implants such as microchips, medicants or other such devices under the skin of animals or humans. The implanter has a tubular implanter body with an interior wall which has a feature for retaining the implant, a hollow needle integral with the implanter body, and a push rod which engages the implant and pushes it through the hollow needle and into the animal or human. One end of the push rod is bent so that when the push rod is operationally disposed in the implanter body, the bent end is forced to become nearly straight, which provides friction force between the push rod and the interior wall of the implanter body to keep the push rod from falling out of the implanter body. The other end of the push rod has a knob which the user manually engages to depress the push rod. An implanter of the present invention accommodates typical manufacturing variations in the inside diameter of the implanter body or of the push rod with imperceptible changes in friction load on the push rod.

5 Claims, 2 Drawing Sheets

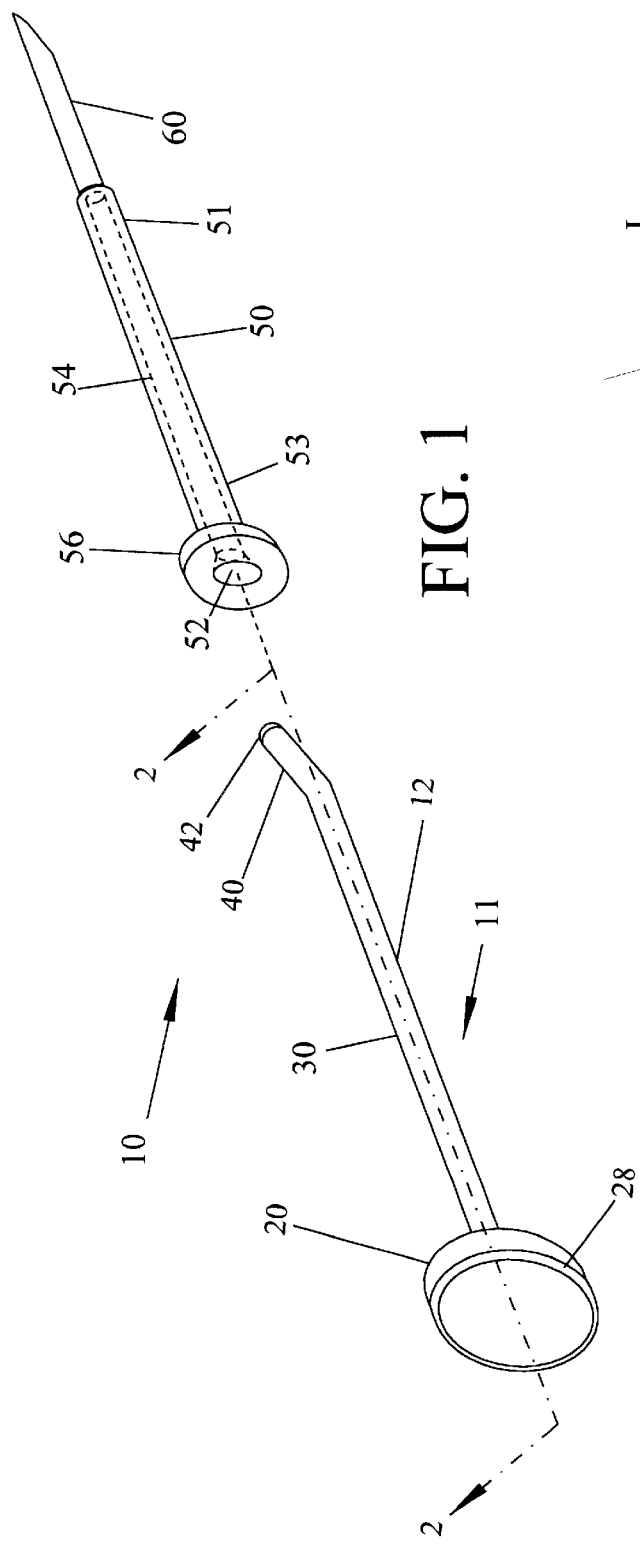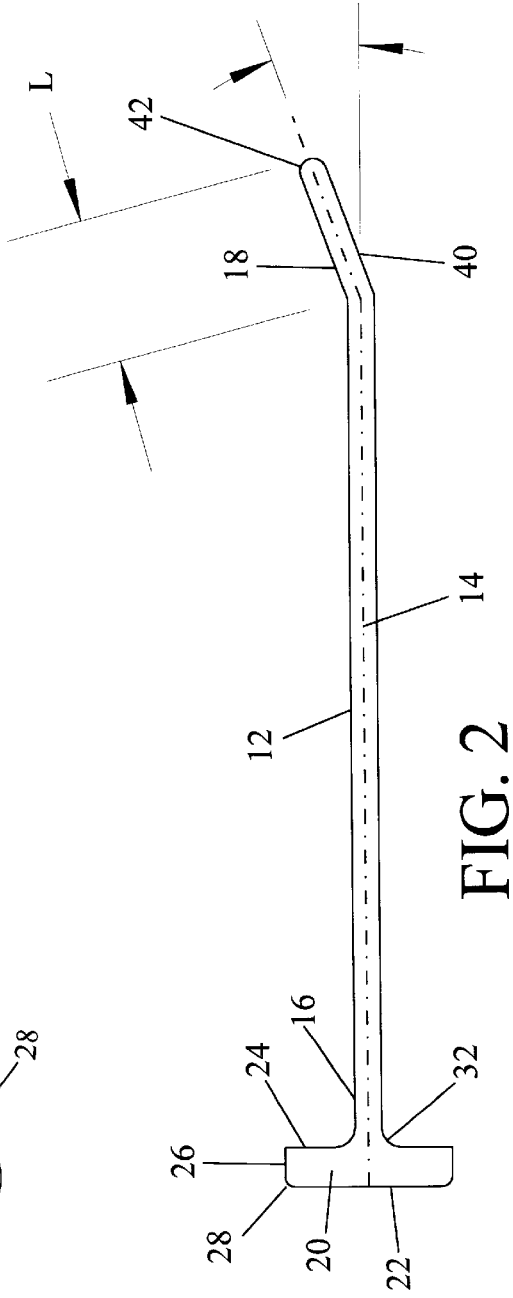

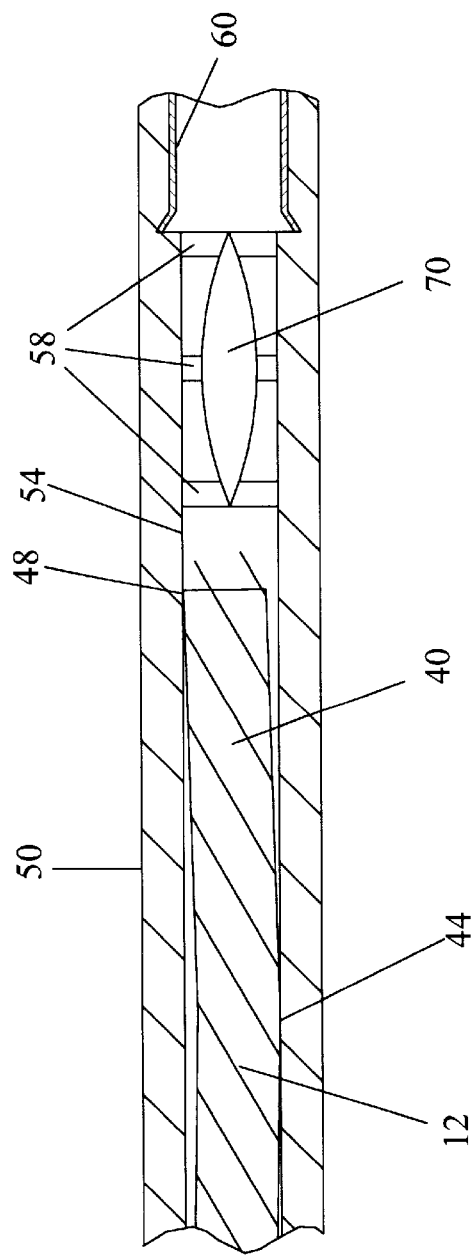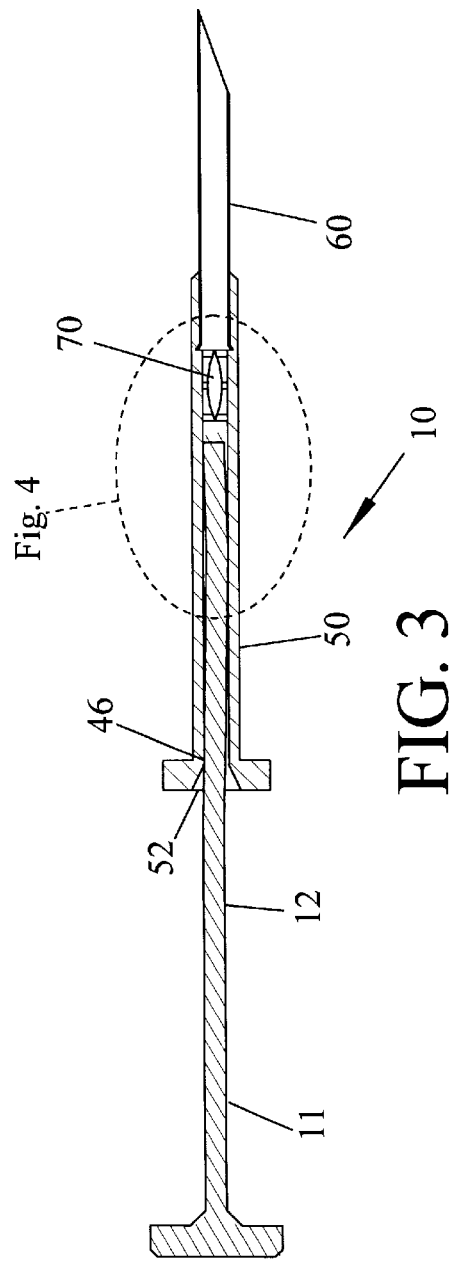

DEVICE FOR IMPLANTING ARTICLES UNDER SKIN

BACKGROUND OF THE INVENTION

1. Field of the Invention

The present invention pertains generally to veterinary medical devices. More particularly, the invention pertains to implant delivery devices. However, the invention also may be useful in other applications.

2. Background Information

Electronic integrated circuit microchips and chemical medicants have been developed which can be implanted under the skin of an animal or human. Microchips carry coded information which can be used, for example, to identify an animal when the chip is scanned. This is useful to help owners recover stray animals. The chip, or implant, may also contain information such as the animal's or human's medical history, or relevant commercial information.

Veterinary medicants, or potential medicants include time delayed pharmaceuticals, nutritional supplements, growth stimulants, hormones, antibodies, antigens, biologics and vaccines.

Microchips and medicants could also be implanted under the skin of humans. Microchips could contain identifying information which may be useful in detecting abducted children or run-away children. Microchips could also contain vaccination and medical information which could be useful to school personnel. For adults a microchip could contain information that alerts a doctor that the person is epileptic or diabetic. Such information is currently conveyed by devices such as medic alert bracelets, but since such devices are easily separable from the person, they can be lost or forgotten and the critical information may not be available when needed.

Medicants or potential medicants include nutritional supplements, and disease prevention and/or treatments, and birth control substances.

One device used to implant a microchip or medicant is a syringe-like device comprising a tubular implanter body with an interior wall which has a feature for retaining the implant, a hollow needle integral with the implanter body, and a push rod which installs inside the implanter body, engages the implant, and pushes it through the hollow needle and into the animal or human. Three partial-circumference friction ribs on the interior wall of the implanter body near the base of the needle hold the implant in place in the implanter body. The internal diameter of the hollow needle is approximately 0.1", that of the interior wall of the implanter body is 0.101±.005 inches, and the friction ribs have an internal diameter of approximately 0.090 inches. The push rod has an outside diameter of 0.087+0.005 inches.

To keep the push rod from falling out of the implanter body, in a prior art implanter, the push rod has three partial-circumference friction ribs. The ribs on the push rod are 0.101 to 0.103 inches in diameter. Under ideal conditions, the ribs of the push rod would have a friction fit with the interior wall of the implanter body. The friction fit would be sufficiently tight so that the push rod would not fall out under normal use, but not so tight that it creates significant resistance when the push rod is depressed to insert the implant.

However, the manufacturing tolerance on the implanter body allows the diameter of the interior wall to range from 0.096 to 0.106 inches. When the interior wall diameter is greater than 0.103 inches, the friction ribs do not engage the interior wall of the implanter body and the push rod can fall out. When the diameter of the interior wall is less than 0.098 inches, unnecessary additional load is required to depress the push rod.

There is no adjustment for fit between the push rod and implanter body. It is not practical to mix and match individual push rods and implanter bodies to achieve optimum fit among all of them. To tighten the manufacturing tolerance on the interior wall of the implanter body would be costly.

Despite the need in the art for an implanter which overcomes the disadvantages of the prior art, none insofar as is known has been developed.

Accordingly, it is an object of the present invention to provide an improved implanter which has a push rod which will not fall out of an implanter body. It is a further object of the invention to provide an improved implanter which readily accommodates manufacturing variations in both the inside diameter of implanter bodies and the outside diameter of push rods. It is a further object of the invention to provide an improved implanter which makes the load required to depress the push rod insensitive to the manufacturing variation of the inside diameter of implanter bodies or the outside diameter of the push rod.

BRIEF SUMMARY OF THE INVENTION

The apparatus of the present invention provides an improved implanter for inserting implants such as microchips, medicants or other such devices under the skin of animals or humans. The implanter has a tubular implanter body with an interior wall which has a feature for retaining the implant, a hollow needle integral with the implanter body, and a push rod which engages the implant and pushes it through the hollow needle and into the animal or human. One end of the push rod has a knob which the user manually engages to depress the push rod. The other end of the push rod has a minor portion consisting of the last approximately ½ inch segment bent approximately 20° from the axis of the remaining major portion, which is straight. When the push rod is operationally disposed in the implanter body, the bent end is forced to become nearly straight, which induces a bending load in the push rod causing three-point contact with the interior wall of the implanter body. The contact between the push rod and the interior wall of the implanter body provides friction force to keep the push rod from falling out of the implanter body. An implanter of the present invention accommodates typical manufacturing variations in the inside diameter of the implanter body or of the implanter push rod with imperceptible changes in friction load on the implanter push rod.

The features, benefits and objects of this invention will become clear to those skilled in the art by reference to the following description, claims and drawings.

BRIEF DESCRIPTION OF THE SEVERAL VIEWS OF THE DRAWING

FIG. 1 is a perspective view of an implanter of the present invention with the push rod disengaged from the implanter body.

FIG. 2 is a longitudinal sectional view of the push rod taken along line 2—2 of FIG. 1.

FIG. 3 is a longitudinal section view of an implanter of the present invention with the push rod engaged in the implanter body.

FIG. 4 is an enlarged view of the highlighted area of FIG. 3.

DETAILED DESCRIPTION

Referring to the drawings, wherein like reference numerals designate like or similar elements throughout, a preferred embodiment of the implanter 10 is illustrated in FIGS. 1–4.

Referring to FIG. 1, implanter 10 is comprised of a push rod 11 and a syringe-like tubular body 50 having an interior wall 54, an integral hollow needle 60 on its distal end 51, and a flange 56 and tapered orifice 52 on its proximal end 53 end which receives push rod 11. Referring to FIGS. 1 and 2, push rod 11 comprises a rod element 12 having a straight portion 30 and a bent portion 40 with tip 42 at its distal end 18 and a knob 20 attached to its proximal end 16. Push rod 11 is installed in body 50 by inserting tip 42 of bent portion 40 into tapered orifice 52 and pushing push rod 11 along interior wall 54. When bent portion 40 is all the way past orifice 52, bent portion 40 must straighten to allow the straight portion 30 of rod element 12 to enter orifice 52. As bent portion 40 straightens, push rod 11 can be advanced distally along interior wall 54 of body 50.

In the preferred embodiment, the total length of push rod 11 is 3.36 inches, the outside diameter of rod element 12 is approximately 0.087 inches. In the preferred embodiment, rod element 12 has a round cross section, but rod element 12 may have any cross sectional shape.

Knob 20 has a proximal face 22, a distal face 24, and a circumferential surface 26. A radius 28 blends proximal face 22 with circumferential surface 26, and radius 32 blends distal face 24 with proximal rod end 16. In the preferred embodiment, knob 20 is approximately ½ inch diameter with a thickness of approximately ⅛.

Rod element 12 has a central axis 14. Bent portion 40 of distal end 18 of rod element 12 is of length L is bent at an angle θ from axis 14. In the preferred embodiment length L is approximately ½ inch, and angle θ is approximately 20°. Length L can be greater or less than ½ inch and the bend angle θ can be greater or less than 20°. The combination of length L and bend angle θ along with mechanical properties of rod element 12 determine the frictional load resulting between push rod 11 and interior wall 54 of body 50. If the combination of these factors is such that it is very difficult to straighten bent portion 40, it will be difficult to install push rod 11 in body 50, and the friction between push rod 11 and interior wall 54 may be undesirably high. If the combination of factors is such that it is very easy to straighten bent portion 40, it will be very easy to install implanter push rod 11 in body 50, however, the friction loads may not be high enough to keep push rod 11 from falling out of body 50.

The material from which rod element 12 is made should have sufficient creep resistance so that bending loads induced by straightening bent portion 40 will not severely relax over time, which could allow push rod 11 to fall out of body 50. The preferred material for rod element 12 is plastic such as polypropylene. The preferred method of construction of push rod 11 is to mold it as a single unit.

Also in the preferred embodiment, tip 42 of bent portion 40 has a fill radius to help facilitate insertion of push rod 11 into body 50 and to facilitate smooth travel of tip 42 against the interior wall 54 of body 50.

Referring to FIGS. 3 and 4, implanter 10 is shown with implant 70 and push rod 11 installed in body 50 having a needle 60. Three friction ribs 58 located proximally of needle 60 on interior wall 54 hold implant 70 in place. In the preferred embodiment, friction ribs 58 are partial circumference structures approximately 0.02 inches wide extending inward from wall 54 approximately 0.005 inches and spaced at approximately 0.1 inch increments. Implant 70 is inserted into orifice 52 and slid along interior wall until implant 70 engages friction ribs 58. Push rod 11 can advance implant 70 along interior wall 54 until implant 70 engages friction ribs 54. To install push rod 11 in body 50, bent portion 40 is inserted into orifice 52 of body 50 and push rod 11 is pushed along interior wall 54 of body 50. The user can feel the implant engage the friction ribs. Both implant 70 and push rod 11 will remain installed in body 50 without falling out due to normal handling of implanter 10.

During installation of push rod 11, bent portion 40 of rod element 12 is forced to substantially straighten to fit within the space formed by interior wall 54. The inherent stiffness of straight portion 30 and bent portion 40 of rod element 12 and causes rod element 12 to sustain bending loads which cause rod element 12 to contact interior wall 54 at points 44, 46, and 48. The material properties and stiffness of rod element 12 determine the bending loads in rod element 12, and the friction force imparted on rod element 12 from interior wall 54. The material properties of the relatively stiff body 50 induce bending of the relatively less stiff bent portion 40 of the rod 12 when it is located within the interior wall 54.

Significant bending loads are introduced in rod element 12 by deflecting bent portion 40 nearly 20° in the preferred embodiment. Any typical manufacturing variation in the diameter of interior wall 54 will cause that bending angle to vary only a fraction of a degree and will not significantly change the bending loads in rod element 12. This gives implanter 10 the ability to accommodate typical manufacturing variations in the diameter of the body 50 or of the push rod 11 with imperceptible changes in friction load on the implanter push rod 11 as it is depressed.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. An implanter for implanting microchips, medicants, or other articles under the skin of animals or humans comprising:

(a) a body having a tubular structure with a distal end, a proximal end, and an interior wall defining a central bore for receiving a push rod and an article to be implanted;

(b) a hollow needle attached to said distal end of said body and extending distally from said body; and (c) a push rod having:

(i) a rod element having a central axis, a proximal end and a distal end, said distal end of said rod element having a length bent away from said central axis; and (ii) a knob element disposed on said proximal end of said rod element; said push rod being received by said central bore of said body at said proximal end of said body, said push rod being operationally disposed in said central bore of said body whereby said interior wall of said body induces bending of said bent length of said distal end of said push rod to cause said push rod to be frictionally retained against said interior wall of said body.

2. The implanter of claim 1 wherein said body has a feature on said interior wall between said distal of said body end and said proximal end of said body for retaining said article to be implanted.

3. The implanter of claim 2 wherein said feature for retaining said article to be implanted is at least one rib extending inward from said interior wall.

4. A method of using an implanter comprising the steps of:
   (a) providing an implanter having
   (i) a body having a tubular structure with an interior wall defining a central bore, a distal end and a proximal end,
   (ii) a hollow needle attached to said distal end of said body and extending distally from said body,
   (iii) a push rod having a knob element and a rod element, said rod element having a central axis, a proximal end and a distal end, said distal end of said rod element having a length bent away from said central axis, said knob element being disposed on said proximal end of said rod clement;
   (b) inserting said bent length of said distal end of said push rod into said central bore of said body at the proximal end of said body;
   (c) causing said bent length to substantially straighten to substantially align with said central axis of said rod element as said push rod is advanced along said interior wall of said body so that bending is induced in said push rod which causes friction between said push rod and said interior wall of said body sufficient to retain said push rod in said central bore of said body.

5. An improved implanter device for implanting microchips, medicants, or other articles under the skin of animals or humans, said implanter device having a tubular body with an interior wall defining a central bore, a distal end, a proximal end, a hollow needle attached to said distal end of said body and extending distally from said implanter body, a push rod having a knob element and a rod element, said rod element having a central axis, a proximal end and a distal end, said knob element being disposed on said proximal end of said rod element, said distal end of said rod element being installed in said bore of said body from said proximal end of said body and advanced along said interior wall of said body, wherein the improvement comprises the distal end of said rod element having a length of said rod element bent away from said central axis such that when said push rod is installed in said central bore of said body, said length substantially straightens to substantially align with said central axis of said rod element as said push rod is advanced along said interior wall of said body so that bending is induced in said push rod which causes friction between said push rod and said interior wall of said body sufficient to retain said push rod in said central bore of said body.

* * * * *